US008000984B2

(12) United States Patent
Hasan et al.

(10) Patent No.: US 8,000,984 B2

(45) Date of Patent: Aug. 16, 2011

(54) SYSTEM FOR COMMUNICATION OF HEALTH CARE DATA

(75) Inventors: Malik M. Hasan, Las Vegas, NV (US); J. Dominic Wallen, Tucson, AZ (US); John C. Peterson, Tucson, AZ (US); Cindy A. Post, Colton, CA (US); Ralph A. Korpman, San Bernardino, CA (US)

(73) Assignee: HealthTrio LLC, Centennial, CO (US)

( * ) Notice: Subject to any disclaimer, the term of this patent is extended or adjusted under 35 U.S.C. 154(b) by 0 days.

(21) Appl. No.: 12/693,522

(22) Filed: Jan. 26, 2010

(65) Prior Publication Data

US 2010/0179836 A1 Jul. 15, 2010

Related U.S. Application Data

(60) Division of application No. 11/603,399, filed on Nov. 22, 2006, which is a continuation of application No. 10/381,158, filed as application No. PCT/US01/42618 on Oct. 11, 2001, now Pat. No. 7,720,691.

(60) Provisional application No. 60/239,860, filed on Oct. 11, 2000.

(51) Int. Cl.
*G06Q 10/00* (2006.01)

(52) U.S. Cl. ..................................... 705/3; 705/2; 705/4

(58) Field of Classification Search ....................... 705/3
See application file for complete search history.

(56) References Cited

U.S. PATENT DOCUMENTS

| | | | | |
|---|---|---|---|---|
| 4,491,725 | A * | 1/1985 | Pritchard | 705/2 |
| 5,065,315 | A * | 11/1991 | Garcia | 705/2 |
| 5,664,109 | A * | 9/1997 | Johnson et al. | 705/2 |
| 5,737,539 | A * | 4/1998 | Edelson et al. | 705/3 |
| 5,772,585 | A * | 6/1998 | Lavin et al. | 600/300 |
| 5,845,255 | A * | 12/1998 | Mayaud | 705/3 |
| 6,032,119 | A * | 2/2000 | Brown et al. | 705/2 |
| 6,076,166 | A * | 6/2000 | Moshfeghi et al. | 726/4 |
| 6,208,973 | B1 * | 3/2001 | Boyer et al. | 705/2 |
| 6,347,329 | B1 * | 2/2002 | Evans | 709/202 |
| 6,988,075 | B1 * | 1/2006 | Hacker | 705/3 |
| 7,664,660 | B2 * | 2/2010 | Korpman et al. | 705/2 |
| 2003/0208382 | A1 * | 11/2003 | Westfall | 705/3 |

OTHER PUBLICATIONS

Americans with Disabilities Act of 1990 (ADA).*

Masys et al., Patient Centered Access to Secure Systems Online (PCASSO): a Secure Approach to Clinical Data Access Via the World Wide Web, Proc. AMIA Annual Fall Symp. 1997: 340-343.*

* cited by examiner

*Primary Examiner* — Dilek Cobanoglu
*Assistant Examiner* — Michael Fuelling
(74) *Attorney, Agent, or Firm* — Barnes & Thornburg LLP

(57) ABSTRACT

An apparatus for communicating health care data from a sender to a receiver is provided. The apparatus has a first computer system, a second computer system, and a rules engine. The first computer system has health care data stored therein. The second computer system is in operable communication with, and is configured to extract the health care data from, the first computer system. The rules engine normalizes the extracted health care data to a predefined format. The rules engine defines a plurality of health care data fields in the predefined format, as well as a plurality of relationships between fields of normalized data.

13 Claims, 12 Drawing Sheets

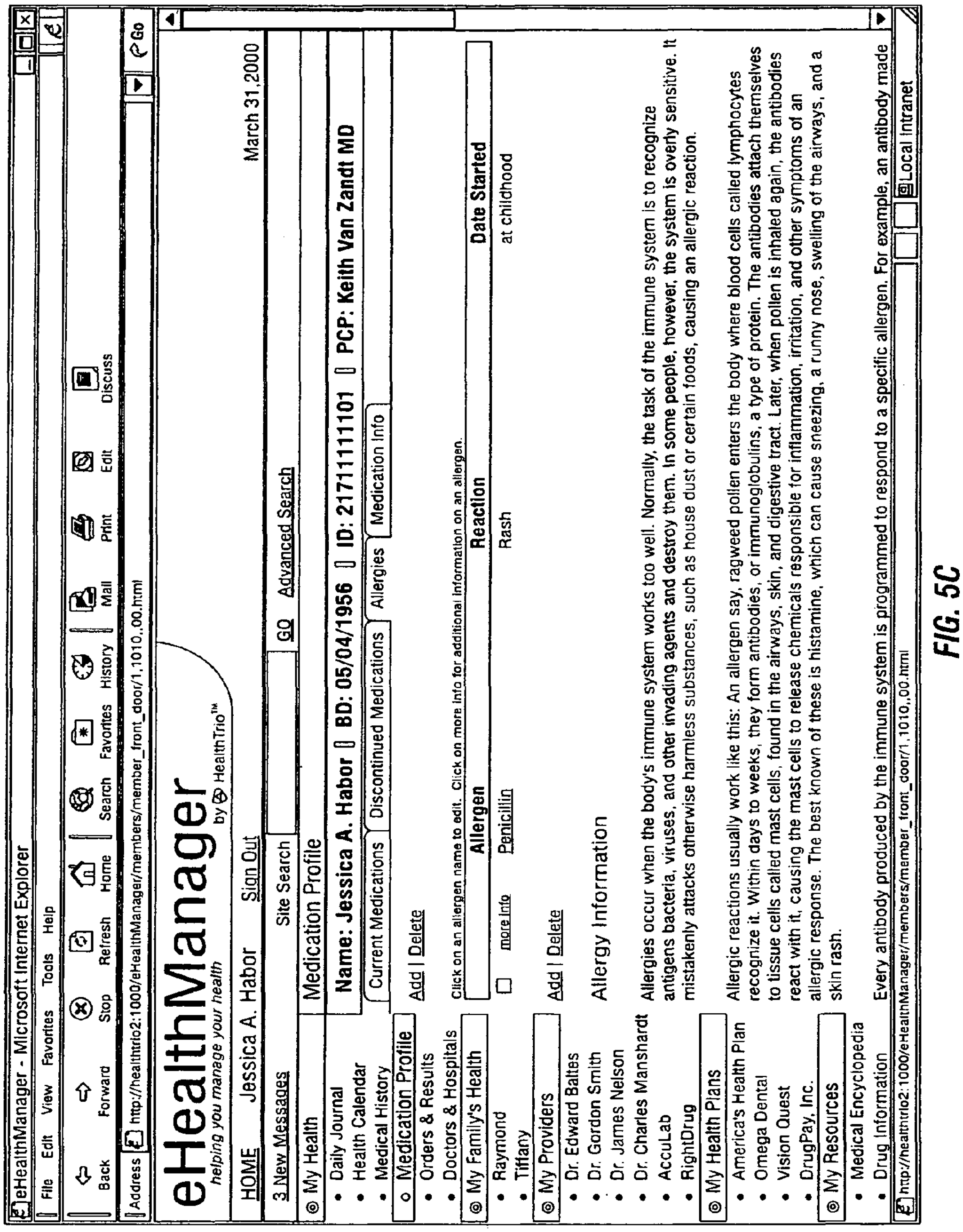

FIG. 5C eHealthManager
*helping you manage your health*  by HealthTrio™

HOME   Jessica A. Habor   Sign Out

Site Search [ ]   GO   Advanced Search                                                                       March 31, 2000

Medication Profile

Name: Jessica A. Habor  |  BD: 05/04/1956  |  ID: 21711111101  |  PCP: Keith Van Zandt MD

| Current Medications | Discontinued Medications | Allergies | Medication Info |

Add | Delete

Click on an allergen name to edit. Click on more info for additional information on an allergen.

| | Allergen | Reaction | Date Started |
|---|---|---|---|
| ☐ more info | Penicillin | Rash | at childhood |

Add | Delete

Allergy Information

Allergies occur when the body's immune system works too well. Normally, the task of the immune system is to recognize antigens bacteria, viruses, and other invading agents and destroy them. In some people, however, the system is overly sensitive. It mistakenly attacks otherwise harmless substances, such as house dust or certain foods, causing an allergic reaction.

Allergic reactions usually work like this: An allergen say, ragweed pollen enters the body where blood cells called lymphocytes recognize it. Within days to weeks, they form antibodies, or immunoglobulins, a type of protein. The antibodies attach themselves to tissue cells called mast cells, found in the airways, skin, and digestive tract. Later, when pollen is inhaled again, the antibodies react with it, causing the mast cells to release chemicals responsible for inflammation, irritation, and other symptoms of an allergic response. The best known of these is histamine, which can cause sneezing, a runny nose, swelling of the airways, and a skin rash.

Every antibody produced by the immune system is programmed to respond to a specific allergen. For example, an antibody made

*Sidebar navigation:*
- 3 New Messages
- ⊙ My Health
  - Daily Journal
  - Health Calendar
  - Medical History
  - ○ Medication Profile
  - Orders & Results
  - Doctors & Hospitals
- ⊙ My Family's Health
  - Raymond
  - Tiffany
- ⊙ My Providers
  - Dr. Edward Baltes
  - Dr. Gordon Smith
  - Dr. James Nelson
  - Dr. Charles Manshardt
  - AccuLab
  - RightDrug
- ⊙ My Health Plans
  - America's Health Plan
  - Omega Dental
  - Vision Quest
  - DrugPay, Inc.
- ⊙ My Resources
  - Medical Encyclopedia
  - Drug Information

SYSTEM FOR COMMUNICATION OF HEALTH CARE DATA

RELATED APPLICATIONS

This is a divisional application of U.S. application Ser. No. 11/603,399, filed Nov. 22, 2006, which was a continuation of U.S. application Ser. No. 10/381,158, filed on Oct. 6, 2003 now U.S. Pat. No. 7,720,691, entitled "System for Communication of Health Care Data," which was the National Stage of International Application No. PCT/US01/42618, filed Oct. 11, 2001, entitled "System for Communication of Health Care Data," which claimed the benefit of Provision Application No. 60/239,860 filed on Oct. 11, 2000, entitled "Apparatus and Method for Establishing Connectivity." To the extent not included below, the subject matter disclosed in these applications are hereby expressly incorporated into the present application.

FIELD OF THE INVENTION

The present invention relates generally to a computerized system that establishes connectivity between interested parties in the health care industry for the administration of health care services. More particularly, the present invention relates to a system for the normalization of health care data of various formats and exchanging the data in normalized form between insurers and participants, such as providers, patients, and employers.

BACKGROUND AND SUMMARY

Health care can be defined as an information industry; most of the time and money spent in procuring and delivering health care is spent creating, retrieving, or using information. Expenditures on health care information technology support, for example, have increased from about one billion dollars in 1990 to a projected $20 billion in 2000. Yet, even with these investments, it is believed that almost half of all current health care expenditures continue to be for non-patient care activities; a major share of which is for non-automated information support.

Resources having to be directed to non-patient care activities have been endemic in the health care industry since the 1960's. During the 1990's, however, with the demise of Medicare Cost Reimbursement and the rise of managed care, there has been a major shift in attitude and focus among both physicians and patients. New rules now govern the delivery of medical care and the payment for such care. Whether via preferred provider arrangements, capitation arrangements of endless variety, case management, or "best practice" enforcement, determining what care is allowed, what will be paid by whom, and making sure that the appropriate information is submitted to ensure that the process works are now consuming a major share of both time and financial resources of insurers, providers, and patients.

Health care participants, like providers and employers, regularly deal with a number of health care plans from various health insurers. These participants, however, can only obtain information from the insurance companies in limited ways, often making the acquisition of such information quite burdensome. Participants usually only have the telephone, fax, or letter available as a means of communication with the insurers.

Particularly vexing is the timely availability of information from insurers regarding financial transactions, such as eligibility, claims, and benefits, and basic patient-related information, such as medical tests and prescriptions. For example, a provider may seek information from an insurer via a submission form or telephone call to that insurer. In many cases, however, such information is sought or received after the care has been delivered and the patient has left the provider's office. This may result in the delivery of services that are not authorized or covered by the patient's insurer, or may result in other consequences that might impact the type or cost of the services provided.

Another reason for these difficulties is the recent expansion of the "payor" community. At one time, payors consisted of the government (both federal and state) and large insurance companies. Now, a complex array of self-insured plans, IDN's, IPA's, and PPO's, undertaking full or partial capitation, insurance carve-outs, and the like have radically increased the number of users of, and the need for, current information regarding insureds. Most of these entities, both small and large, do spend considerable sums on information systems. Yet, because of the extent of manual processing that exists despite these systems, costs per claim remain substantial.

In addition, payors incur the wrath of their providers and patients by designing complex rules that are difficult or perceived as impossible to administer or follow. Though contrary to this perception, payors do have an interest in providing timely information to providers, patients, employers, and other participants. Still, a significant percentage of a provider's claims are rejected often because they do not comply with all of the rules. These claims require resubmission, telephone calls, and other expensive manual interventions. The dollar costs for this current processing scheme are high. In fact, an entire clearinghouse industry has been developed to provide eligibility (but not benefits) verification services to providers for a fee. Many of the requested verifications, however, cannot be performed at all by such clearinghouses, and those that are performed are often unacceptably cumbersome and, thus, too expensive.

Referral authorizations are often even more complex than claims and such authorization services are generally not available via traditional clearinghouses. Each time a provider writes a prescription, for example, it is written against a formulary specific to that patient's health care plan established by their insurer. Because there are so many formularies, drug prescriptions, too, are often rejected for payment, causing additional work for both the provider and the patient. Similarly, medical tests must be sent to laboratories contracted to support a particular plan, and are reimbursed only when matching complex medical necessity rules.

Many providers do have practice management systems that track encounters and manage billing. None of these systems, however, have the sophistication to accomplish the task of providing all of the information from all the various health insurers in such a cogent form that can be useful to the provider.

Not only providers, but patients, too, spend a majority of their time interacting with the health care system engaged in non-health care activities. This "wasted" time is virtually all related to scheduling appropriate interventions, to waiting for information or services, or to obtaining authorization, reimbursement, or other information for desired or required health care.

The internet has emerged as a major source of health care information for the public. A substantial portion of internet users use it for health care information or management. Specifically, patients search the internet for medical information and answers related to their area of concern. In fact, it is becoming common for a patient to enter a physician's office armed with printouts and long lists of questions and recommendations from web pages on the internet.

Unfortunately, even with the connectivity the internet provides, information exchange between insurers and patients is lacking. Most of the information available to patients from their insurer is on an automated basis from databases related to either general health care literature or to specific normality support groups. A critical aspect of the patient's health care program, however, is not only knowledge of the normality or support groups, but also what their insurer's health care plan provides as treatment options for that normality, eligibility information, referral authorization, claim submission and payment, testing, and medications. As discussed, these functionalities are too complicated for the current system to handle in an automated environment. Personally-referenced information linked to an individual patient's provider and health care plan is generally unavailable, because that data exists in several databases often each in a different, incompatible format, requiring human intervention to extract and process the data. The patient's current solution is, thus, an endless number of telephone calls at a high cost in dollars, time, and frustration.

A reason for such incompatibility is that each database served the individual needs of those using the data before such a time when connectivity between databases was a consideration. The consequence of having different databases of different formats is that it is not possible to provide a central repository of homogenized data readable by any variety of computers. It is this incompatibility that prevents wide spread connectivity between insurers and participants.

Transliterating and interfacing programs are known in the art. Programs that take data in one format can be translated and read by a computer of a different format. Such transliterating, however, only shifts data from a field of an incompatible format to a target field of a new format. It cannot determine whether the data of the incompatible format is being transferred to the correct target field. Normalization or remodeling of the data not only transfers the data, but also determines the meaning of the data and puts that data in the correct field.

It would, therefore, be beneficial to provide a system with which insurers may communicate with providers, patients, etc., to provide information about a particular health care plan either before, or contemporaneously with, the patient's visit to the provider, regardless the lack of compatibility of the databases. It would be further beneficial if this system of communication spanned a variety of insurers so the provider, for example, may communicate with any plan in which the patient participates. It would also be beneficial for providers to have an automated system of determining eligibility and benefits, receiving authorizations and pre-certifications, submitting claims, obtaining reimbursements, and adjudicating claim problems through the normalization of data of the incompatible databases.

Accordingly, an illustrative embodiment of the present disclosure provides an apparatus for communicating health care data from a sender to a receiver. The apparatus comprises a first computer system, a second computer system, and a rules engine. The first computer system having health care data stored therein. The second computer system is in operable communication with, and is configured to extract the health care data from the first computer system. The rules engine normalizes the extracted health care data to a predefined format. The rules engine defines a plurality of health care data fields in the predefined format, as well as a plurality of relationships between fields of normalized data.

Further embodiments may include the first computer being a plurality of computers each having portions of the health care data stored thereon. The apparatus may also comprise a third computer system, in operable communication with, and configured to receive the normalized data from, the second computer system. The rules engine may determine whether the third computer is authorized to receive the health care data.

Another illustrative embodiment provides a method for communicating health care data from one computer system to another. The method comprises the steps of storing health care data in a first computer system; extracting health care data from the first computer system and communicating the extracted data to a second computer system; normalizing the extracted data to a predefined format in accordance with a rules engine that defines a plurality of health care data fields in the predefined format and a plurality of relationships between fields of normalized data; and communicating the normalized data to a third computer system.

Further embodiments of the illustrative method may include the first computer system comprising a plurality of computers, wherein the storing step includes storing health care data in more than one of said computers. Also, the third computer system comprises a plurality of computers. The health care data exists across a plurality of databases such that each of the plurality of databases are in operable communication with the second computer system.

Another illustrative embodiment provides a system of exchanging health care data between a sender and a receiver. The system comprises a sender computer, an intermediary computer, a rules engine and a receiver computer. The sender computer stores the health care data. The intermediary computer is in operable communication with the sender computer and is configured to extract the health care data. The extracted data is normalized to a predefined format, creating normalized data pursuant to a rules engine. The rules engine defines each field of the health care data and converts each field to a corresponding field in the predefined format. The rules engine also defines how the normalized data should relate to each other pursuant to predetermined instructions. The receiver computer is in operable communication with the intermediary computer. The receiver computer receives the normalized data subjected to the second rules engine.

Further embodiments may include the sender computer being a plurality of computers each having portions of the health care data stored thereon. The rules engine may determine whether the receiver computer is authorized to receive the health care data. When the receiver is a health care provider, the normalized data exchanged between the sender and receiver may be chosen from a group comprising eligibility/benefit display, member roster, claim submission, provider lookup, formulary lookup, diagnosis code lookup, procedure code lookup, access health plan information online, communicate with a health plan on-line, communicate with patients on-line, patient-centric view of data across several health plans, order generation and tracking, results review and release, result printing, prescription writing, medication profile for each patient, access to patient's personal health record based on patient approval, personalized medical and health care content integration, both context-specific and on demand, e-commerce integration: office, medical and health-related product awareness and buying capabilities, email, practice management system subscription, support disease management, and physician credentialing subscription. When the receiver is an employer, the normalized data exchanged between the sender and receiver is chosen from a group comprising group eligibility, group enrollment, enrollment changes, formulary lookup, e-commerce integration, access from health plan web site or direct access via URL, personalized content integration, both context-specific and on demand, e-commerce integration and health care-related product awareness and buying capabilities.

When the receiver is a patient, the normalized data exchanged between the sender and receiver is chosen from a group comprising identification card requests, address changes, provider directory inquiries, personalized health information based on an interest profile, diagnosis information, relevant articles and patient education materials, communications from health care providers and health care plans, lab and radiology results, scheduled appointments with a health care provider, prescription refills, personal health records, eligibility/benefit information, claim information, referral and authorization information and status, provider lookup, family history, medication profile and formulary lookup.

Another illustrative embodiment of the present invention provides a system of normalizing health care data for transfer between an insurer and a participant. The system comprises an insurer system, an intermediary system, and a participant system. The insurer system is configured to maintain at least one database comprising the health care data. The intermediary system is operatively connected to the insurer system and to the database, configured to extract the health care data from the database of the insurer system, and store the health care data in a staging database as extracted data. The extracted data is normalized to a predefined format, creating normalized data pursuant to a rules engine that defines each field of the extracted data in the predefined format. The rules engine also defines how the normalized data relates to each other pursuant to predetermined instructions. The participant system is in operable communication with the intermediary system, and is configured to receive the normalized data subject to the rules engine.

Further embodiments of the illustrative system may include the at least one database being a plurality of databases, such that the intermediary system is operatively connected to the plurality of databases. In addition, the participant system may transmit a request that is sent to the intermediary system that determines which health care data is to be extracted and normalized in order to respond to the request. The participant system may also transmit the request, and the intermediary system may transmit the normalized data over the internet. The rules engine may define the relationships among the normalized data pursuant to predetermined instructions to determine a response to the request. The intermediary system may also comprise an error data system that removes extracted data identified as invalid when the extracted data is normalized. The extracted data identified as invalid is then corrected, reintroduced, and is normalized. The intermediary system may further comprise an audit database to track the activity of the intermediary system.

Another illustrative embodiment of the present invention provides a system of health care management of medical testing administration between an insurer, a medical laboratory, and at least one health care participant. The system comprises a participant computer, an insurer processing system, a rules database, and a laboratory computer. A medical test request is made at the participant computer pursuant to a first predetermined format. The insurer processing system is operatively coupled to the participant's computer, and is through which the medical request is transferred. The processing system is operatively coupled to the rules database to approve the medical test request pursuant to predetermined criteria. The laboratory computer is operatively coupled to the processing system and receives the medical test request if approved by the rules engine. Results of the medical test are transmitted from the laboratory computer to the processing system. The results are further transmitted to an insurer computer that is operatively coupled to the laboratory computer and to participant's computer.

Further embodiments of the illustrative system may include the processing system converting the results of the medical test to a second predetermined format readable by a database stored on the insurer computer. In addition, at least one health care participant may be chosen from a group comprising from a health care provider, an employer, and a patient. Furthermore, the medical test request and the results of the medical test may be transmitted through the internet.

Additional features and advantages of the system will become apparent to those skilled in the art upon consideration of the following detailed descriptions exemplifying the best mode of carrying out the system as presently perceived.

BRIEF DESCRIPTION OF THE DRAWINGS

The illustrative system will be described hereinafter with reference to the attached drawings which are given as non-limiting examples only, in which:

FIGS. 5A-5C show an example portal from which a patient can obtain and submit information.

Corresponding reference characters indicate corresponding parts throughout the several views. The exemplification set out herein illustrates an embodiment of the invention, and such exemplification is not to be construed as limiting the scope of the invention in any manner.

DETAILED DESCRIPTION OF THE DRAWINGS

Figure 1:
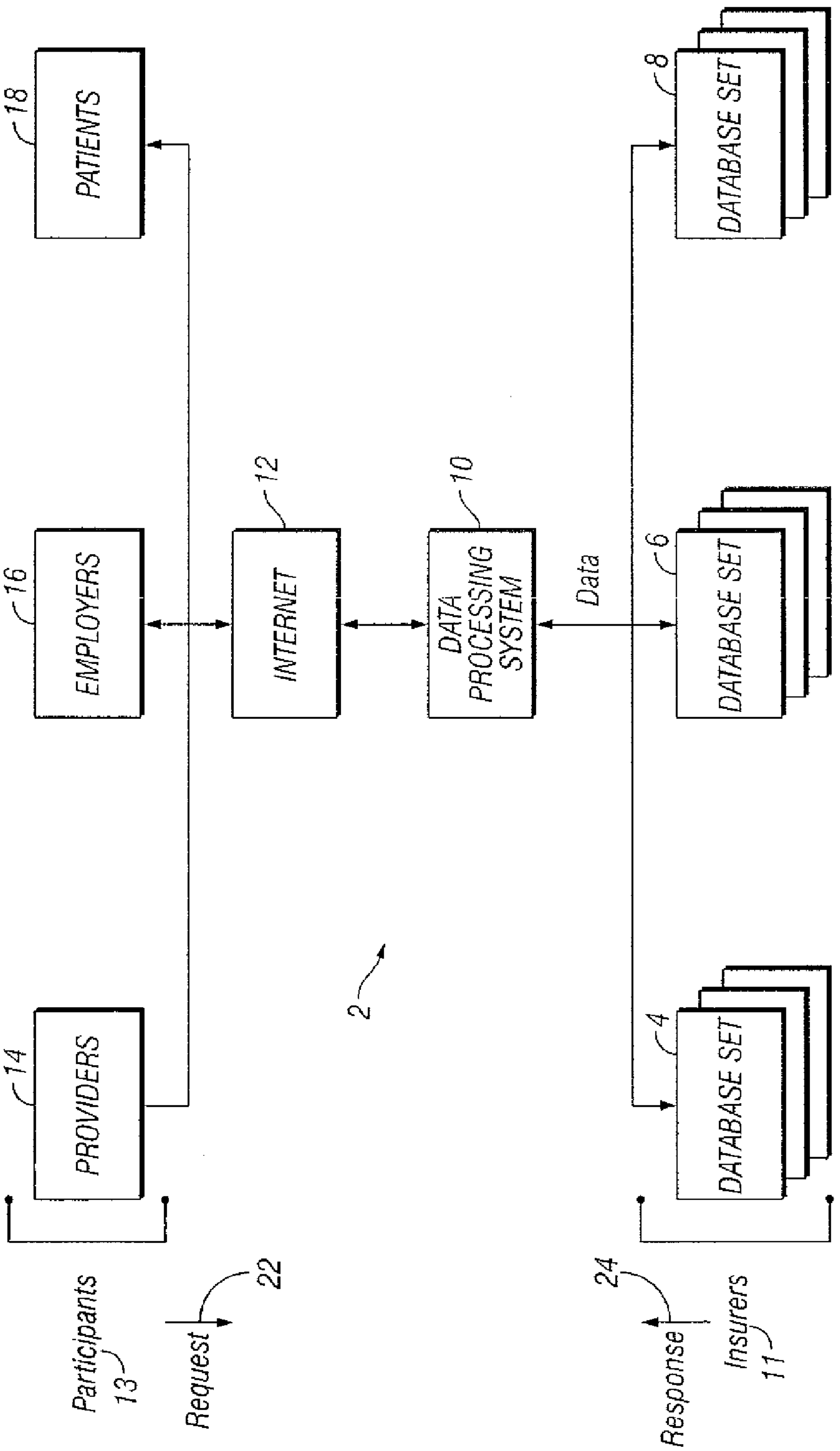
FIG. 1 is a diagrammatic view of a system for normalization of health care data and the exchange of same between several health care insurers and various health care participants.

An illustrative embodiment of the invention, such as that shown in FIG. 1, comprises a system 2 which includes a plurality of database sets 4, 6, 8 offered by a variety of insurers 11. It is appreciated that each health care database set 4, 6, 8 represents an insurer's database processing system or series of processing systems and databases. For example, database sets 4, 6, or 8 may each represent a conventional computer system, a server, a local area network (LAN), a legacy, or other computer system storing one or more databases. It is contemplated that to transmit data, either the system as it exists is capable of doing so, or a system is added to either database sets 4, 6, or 8 to perform this function. It is further contemplated that each of database sets 4, 6, 8 may represent a single database or a plurality of databases, each of which may be of any variety of database formats or languages.

For the purposes of this application, it is contemplated that reference to the term “insurer,” as used herein for insurers 11, is for illustrative purposes only. Such a term includes health insurance companies, but also includes health maintenance organizations, self-insured entities, disease management organizations, capitated health care providers, Medicare agencies, as well as any other organization that might store or manage health care data. The term “insurer” is not to be construed as being limited in scope to only health insurance companies or other “payors.”

Conventionally, health care data is stored on an insurers' computer or series of computers in several databases, each of which often being in a unique format, with each database format being incompatible with other database formats. For example, one insurer may have their health care data stored in one format, and a second insurer may have their health care-related data stored in a second format that is not compatible with the one format. Additionally, and more problematic is that, even within the same insurer's 11 system, eligibility data, for example, may exist in a database of one particular format, developed to suit the needs of its users at the time, whereas, the claims data, for example, may be stored in another database in a format that suits the needs of those users, but with its format being incompatible with the format of the eligibility data. In either example, it is contemplated that in the present invention, health care data of any format is normalized into a common format, and distributed through a common network, like internet 12, to a health care participant 13, who uses the normalized data to conduct health care-related transactions and tasks. It is further contemplated, and to be discussed further herein, that various levels of access and security can be provided to assure that those participants 13 accessing the normalized data are authorized to access only that data predetermined as necessary and appropriate for their particular use or need.

As FIG. 1 shows, data from each database set 4, 6, 8 can be transmitted to a data processing system 10 that normalizes the data into a format readable by particular health care participants 13. More specifically, the data is transmitted over the internet 12, which is operatively connected to and read by participants' 13 computer(s) or terminal(s). Such participants 13 illustratively include providers 14, employers 16, and patients 18, or any combination thereof. It is contemplated that participants 13 can further include any other interested party that can request data or information from an insurer, including other insurers and disease management organizations, for example.

It is contemplated that the transmission of data from database sets 4, 6, or 8 is initiated by any of the participants 13 submitting a request 22 through a computer or computers. Request 22 is transmitted through the internet 12 to data processing system 10 which retrieves the appropriate data from the appropriate database set or sets of either 4, 6, or 8. That data is normalized to a common format, at which point a response 24 to the request 22 is made. For example, a health care provider 14 may place a request 22 on behalf of an insured to authorize payment for a medical procedure. In this example, it is presumed that the data required to formulate a response 24 exists collectively on eligibility, benefits, and claims databases that illustratively exist on database set 4. Data processing system 10, in order to prepare a response 24, determines and extracts which data is necessary from the databases. System 10 then normalizes the data into a homogenous format, and then determines what the nature of the response should be. In this example, response 24 should be to either authorize or deny payment for the medical procedure. System 10 uses the normalized data to determine the response, which is then transmitted to provider 14, thus, completing the transaction. It is contemplated that system 2 may comprise any number of insurers 11 or participants 13. Specifically, data processing system 10, as will be discussed further herein, is able to connect and manage transactions between a single or plurality of participants 13 with any insurer or plurality of insurers 11.

It is further contemplated that system 2 will provide health care participants 13 with a variety of health care transaction options referred to generally in the form of requests 22 and responses 24 between participants 13 and insurers 11. Examples of transactions available to health care providers 14 are: eligibility/benefit display, member roster, claim submission, provider lookup, formulary lookup, diagnosis code lookup, procedure code lookup, access health plan information online, communicate with a health plan on-line, communicate with patients on-line, patient-centric view of data across several health plans, order generation and tracking, results review and release, result printing, prescription writing, medication profile for each patient, access to patient's personal health record based on patient approval, personalized medical and health care content integration, both context-specific and on demand, e-commerce integration: office, medical and health-related product awareness and buying capabilities, email, practice management system subscription, support disease management, and physician credentialing subscription.

As further example, the following are specific records and fields for health care transactions between providers 14 and insurers 11 that utilize normalized data:

Record: Summary
- Fields:
- Activity for (date)
- Referrals
- Test Results
- Members
- Update State for Americas Health
- Benefit Records
- Claim Records
- Patient Records
- Provider Records
- New Just For You Record: Eligibility
- Fields:
- Today's Patients
- Patient Search
- Sex
- Coordination of benefits
- Medicare data
- Add to patient list
- Name
- From Date
- To Date
- Birth date
- Member ID
- Relation
- PCP
- Address
- City
- State
- Zip
- Current Benefit
- Group
- Carrier
- Benefit Plan Record: Claim Status
- Fields:
- Patient Name
- From Date
- To Date
- Claim Number
- Status
- Provider Name
- Patient Name
- Member Number
- Billed Amount
- Patient Responsibility
- Paid Amount
- Date of Service Record: Claim Detail
- Fields:
- Member
- Provider
- Diagnosis
- Description
- Line number
- DOS
- CPT
- Description
- Modifier
- Location
- Units
- Status
- Billed
- Allowed
- Copay
- Coinsurance
- Deductible
- Paid
- Totals Record: Explanation of Payments
- Fields:
- Line Number
- Status Description
- Explanation
- Check/Date Record: Select Specialist
- Fields:
- Address
- City, State, Zip
- Handicap Access
- Office Hours
- Contact
- Phone
- Fax Phone
- Phone After Hours
- Sex
- Birth Date
- Specialty
- Second Specialty
- Accept Patient
- Primary Care
- Board Cert
- Languages
- Hospitals
- Hospital Privileges
- Networks Record: Add Claims
- Fields:
- Health Insurance
- Insured's ID Number
- Patient Last Name
- First Name
- Middle Name
- Patient's Address 1
- Address 2
- City
- State
- Zip
- Patient's Phone
- Birth date
- Gender
- Relationship to Insured
- Marital Status
- Patient Employment Status
- Condition Related to Job
- Con. Rel. to Auto Accident
- Cond. Rel. to Other Accident
- Insured's Last Name
- First Name
- Middle Name
- Gender
- Birth date
- Insured's Address 1
- Address 2
- City
- State
- Zip
- Phone
- Insured's Group or FECA Number
- Insured's Employer/School
- Insured's Insurance Name
- Referring Physician Name
- Referring Physician ID
- Outside lab
- Outside Lab Charges
- Medicaid Resub Code
- Medicaid Orig.
- Prior Auth. Number
- Diag Codes
- Item
- Date From
- Date To
- Place
- Type
- Procedure
- Mod1
- Mod2
- DX Ind.
- Charges
- Days/Units
- Patient
- Provider
- From Date
- To Date
- Diagnosis 1
- Diagnosis 2
- Diagnosis 3
- Diagnosis 4
- Procedure Line
- CPT
- Description
- Amount
- Dx pointer
- Other Errors
- Total Amount
- Billed
- Allowed Amount
- Copay Amount Withheld Amount
Writeoff Amount
Predicted Payment Record: Referral Status
Fields:
Referral Number
Patient (Member ID)
Valid from (months)
Referred by
Referred to
Patient List
Referred by
Referred to
Referral Number
Status Record: Add Referrals
Fields:
Today's Patients
Patient Search
Specialists
Specialist Search
Providers
Diagnosis
Patient
Specialists
Provider
Diagnosis
Start Date
Months Valid
Visits Requested
Reason Record: Procedure and Diagnosis Data
Fields:
Diag Number
Diagnosis Name
Proc Code
Procedure Name
Visits Allowed
Patient
Patient Search
Referred to
Specialist Search
Referred by
Diagnosis
Start Date
Exp Date
Visits Requested
Remarks
Services Requested
Authorized Ancillary Services Record: Diagnosis Codes
Fields:
Diagnosis Code
DX Code
Diagnosis Code Description Record: Procedure Codes
Fields:
Procedure Codes
Procedure Code
Procedure Description
Age From
Age To
Sex
Location Code Record: Drug Therapeutic Class Listing
Fields:
Therapeutic Class
Class Description
Count of Drugs in this Class Record: Formulary List by Therapeutic Class
Fields:
Drug Name
Generic Name
Drug Class
Therapeutic Class
NDC Record: Write Prescription
Fields:
Today's Patients
Patient Search
Providers
For
Medication
Dispense
Refill
Sig: Take
Sig: For
Instructions
Select Pharmacy Record: Medication Profile
Fields:
Type
Medication
Dose
Frequency
Reason
Status Record: Discontinued Medications
Fields:
Type
Medication
Dose
Frequency
Reason
Status Record: Allergies
Allergen
Reaction
Date Started Record: Medical Test Orders
Fields:
Patient ID
Patient Name
Provide ID
Provider Name
Location
Lab Name
Dx
Action
Battery
Test
ID
Type
Volume
Date
Time
Collected By
Chemistry
Hematology
Toxicology/Therapeutics
Microbiology/Virology
Immunology/Serology
Urinalysis/Fluids
Procedure When
Priority
Specimen
Alert
Record: Results
Fields:
Status
Order number
Test Procedure
Alert
Order Date
Facility
Patient
Provider
Date/Time
Procedure
Status
Indicator
Date/Time
Performed
Specimen Number
Type
Status
Result
Value
Desired Range Each field listed above represents data that can exist anywhere on database sets 4, 6, or 8, and be in any format or language. If any request 22 is made which calls up one or more of the above records, data processing system 10 searches, extracts, and normalizes the data so it appears in the correct field in the record. It is appreciated that provider 14 may change the data, if necessary, and transmit it back through internet 12 and data processing system 10 to be stored on the appropriate database set 4, 6, or 8.

Examples of transactions available to employers 16 are: group eligibility, group enrollment, enrollment changes, formulary lookup, e-commerce integration, access from health plan web site or direct access via URL, personalized content integration, both context-specific and on demand, e-commerce integration: human resource, business (e.g., office supplies) and health care-related product awareness and buying capabilities.

Again, as a further example, the following are specific records and fields for health care transactions between employers 16 and insurers 11 that utilize normalized data:

Record: Open Enrollment
Fields:
Health Insurance
Employer Group Number
Last Name
First Name
Middle Name
Employee Address 1
Address 2
City
State
Zip
Home Phone
Work Phone
Primary Language
Birth date
Gender
Social Security Number
Primary Care Physician
Established Patient
Dependent Last Name
First Name
Middle Initial
Birth date
Gender
Relationship
Social Security Number
Primary Care Physician
Established Patient
Effective Date
Hire/Rehire Date
Other Health Care Policy
Name and Address of Insurer
Effective date of other coverage
Policy Holder's Last Name
First Name
Middle Name
Policy/Group Number
Covered by Medicare
Medicare Number(s)
Health insurance within the last 18 months
If yes, type of coverage: group, individual, COBRA, Medicare/Champus,
Conversion or Other
Reason coverage was terminated
Read and Agree to Authorization Statement Record: Enrollment—Changes
Fields:
Health Insurance
Employer Group Number
Last Name
First Name
Middle Name
Employee Address 1
Address 2
City
State
Zip
Home Phone
Work Phone
Primary Language
Birth date
Gender
Social Security Number
Primary Care Physician
Established Patient
Term Member
Dependent Last Name
First Name
Middle Initial
Birth date
Gender
Relationship
Social Security Number
Primary Care Physician
Term Dependent
Hire/Rehire Date
Effective Date
Change Reason
Name
Enrollment Type
Remarks Examples of transactions available to patients 18 are: identification card requests, address changes, provider directory inquiries, and personalized health information based on the member's interest profile, as well as diagnosis information from health plan administrative and clinical information, relevant articles and patient education materials, communications from health care providers and health care plans, lab and radiology results to patients online, scheduled appointments with a health care provider, referral status, prescription refills, education materials, personal health records so it can be maintained in his or her comprehensive health history online for physician reference, view eligibility/benefit information, view claim information, view referral and authorization information, provider lookup, personal health record, family history, medication profile, formulary lookup, and communications between member and provider.

By way of another example, the following may be performed on-line by the patient:

PCP changes

Identification card request

Address changes

Provider directory inquiries

Personalized health information! Based on the member's interest profile as well as diagnosis information from health plan administrative and clinical information, relevant articles and patient education materials will be available in the "News Just For You" section.

Important communication from health care providers and the health plan! Physicians will have the capability to release lab and radiology results to patients on-line. Office staff can notify patients of their scheduled appointments. In addition, a member will receive information on health plan wellness programs and benefit changes that are relevant to that member.

Referral status is accessible to members on-line! This eliminates the time members spend tracking referral status.

Prescriptions can be refilled on-line.

A list of all prescribed and OTC medications can be maintained on-line for review.

Patient education materials are available to advise the member of drug warnings for his or her prescriptions.

Personal health records can be maintained on-line! A member can maintain his or her comprehensive health history on-line for physician reference.

Physician office visits can be scheduled on-line!

In some embodiments, all sources of information (multiple health plans, labs, etc.) are integrated into a single patient referenced database. For example, both providers and patients could use the same database with different views. In some cases the system 10 may provide a health portal for patients. The portal may provide personalized health information based on a patient's claims history, as well as ancillary (lab and pharmacy) information, and business-to-consumer e-commerce including access to Plan information such as eligibility and claim status. Because of the unique advantages offered to patients, this patient base can cost effectively be turned into a large number of registered users in a short period of time. In some cases, relevant articles and patient education materials may be available based on the patient's interest profile, as well as diagnosis information from health plan administrative and clinical information. By way of another example, patients may benefit from health promotion and prevention programs lead by their health plans. For example, patient education about routine mammograms can be provided to the patients meeting target criteria impacting medical management, disease management, and NCUA measurements.

Figure 5A:
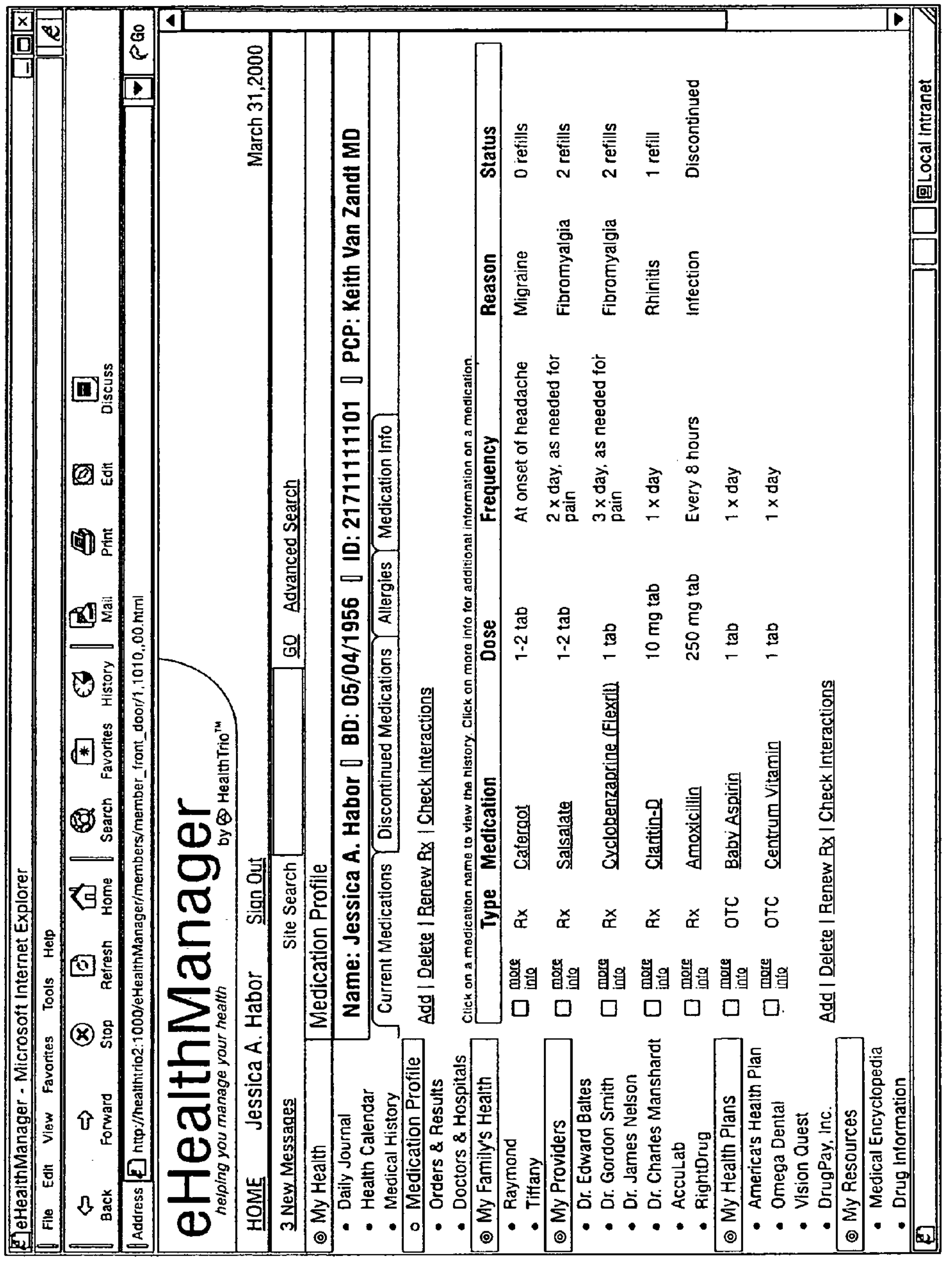
Figure 5B:
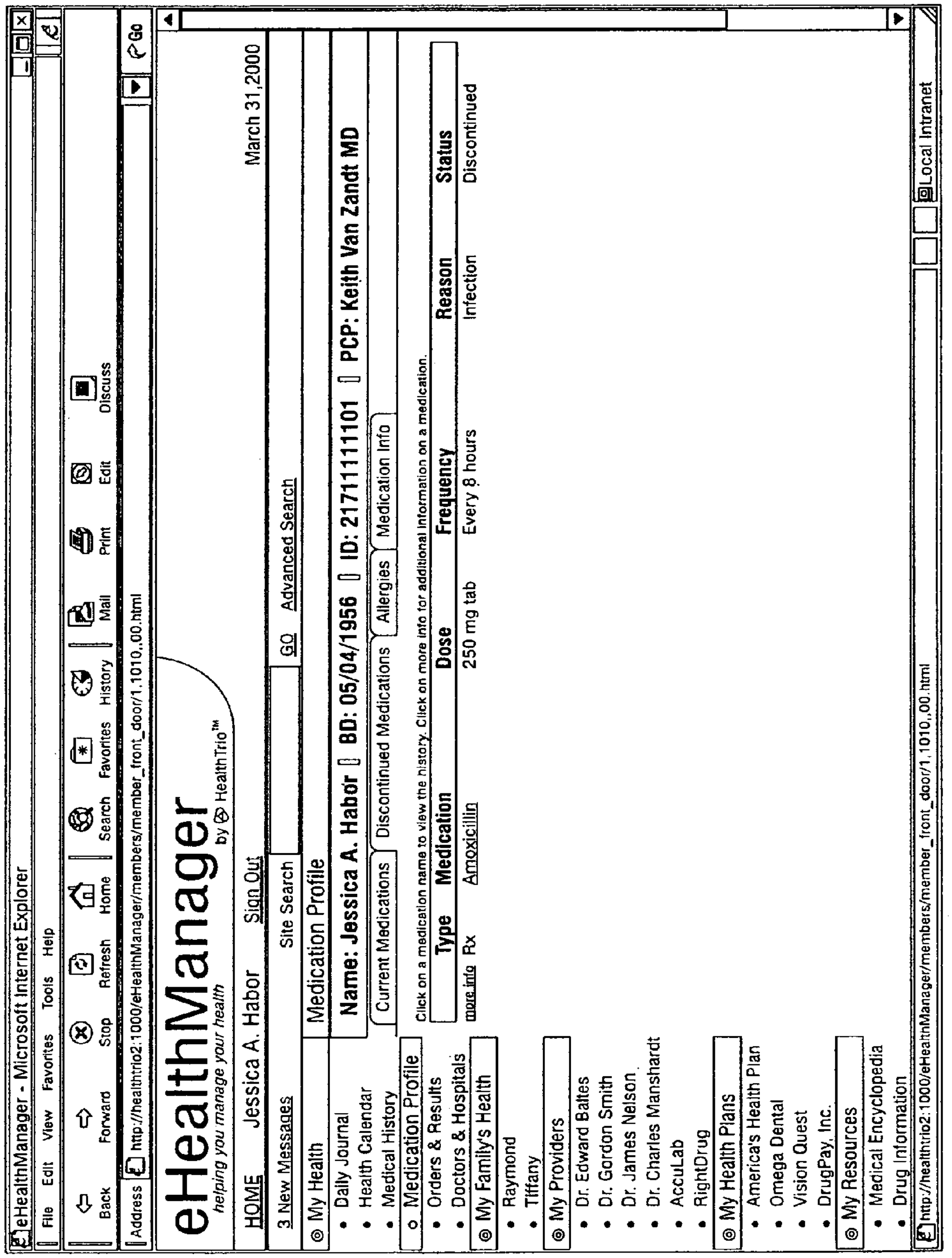
Figure 6A:
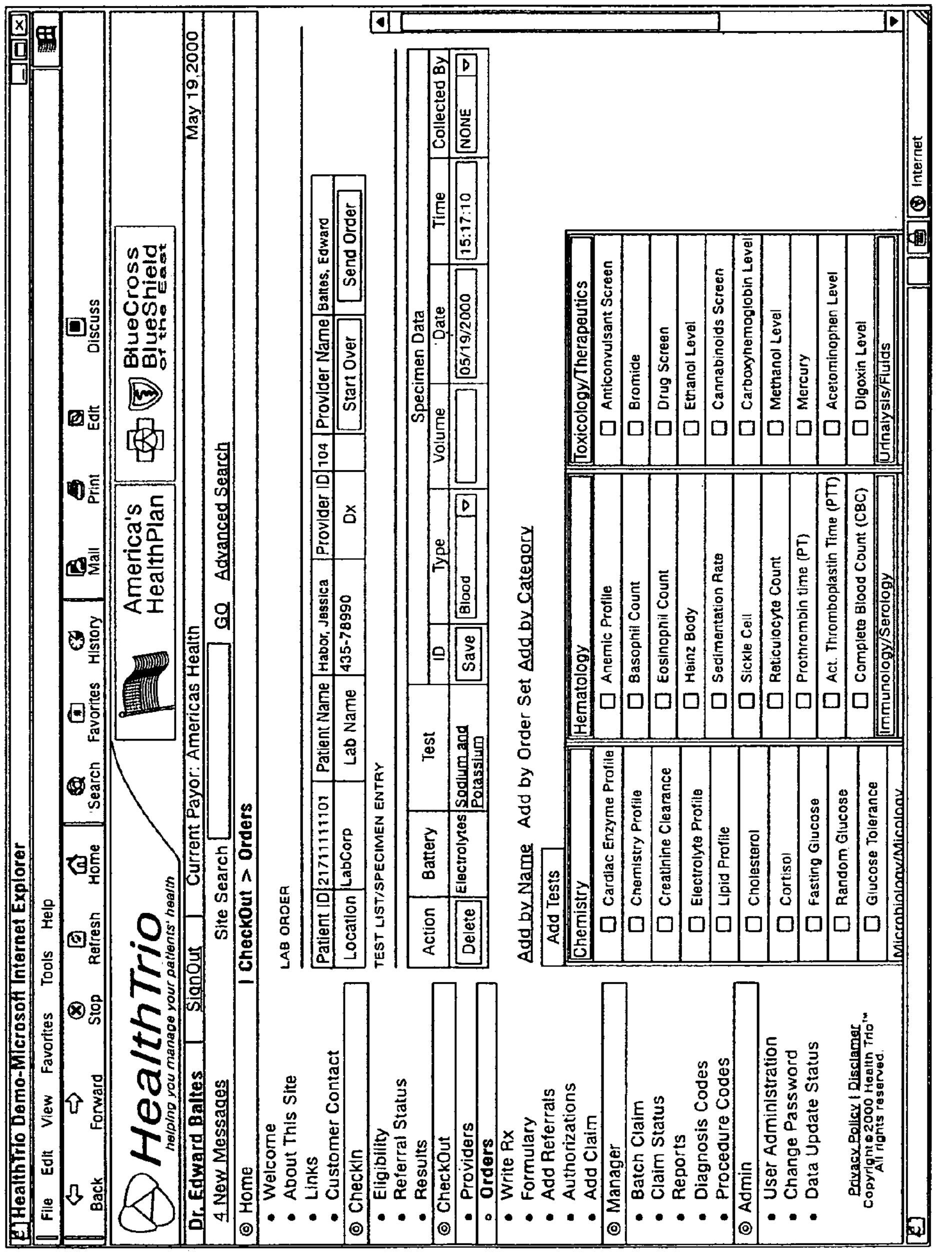
FIGS. 6A-6D show an example user interface for health care providers to order and view medical tests over the Internet.
Figure 6B:
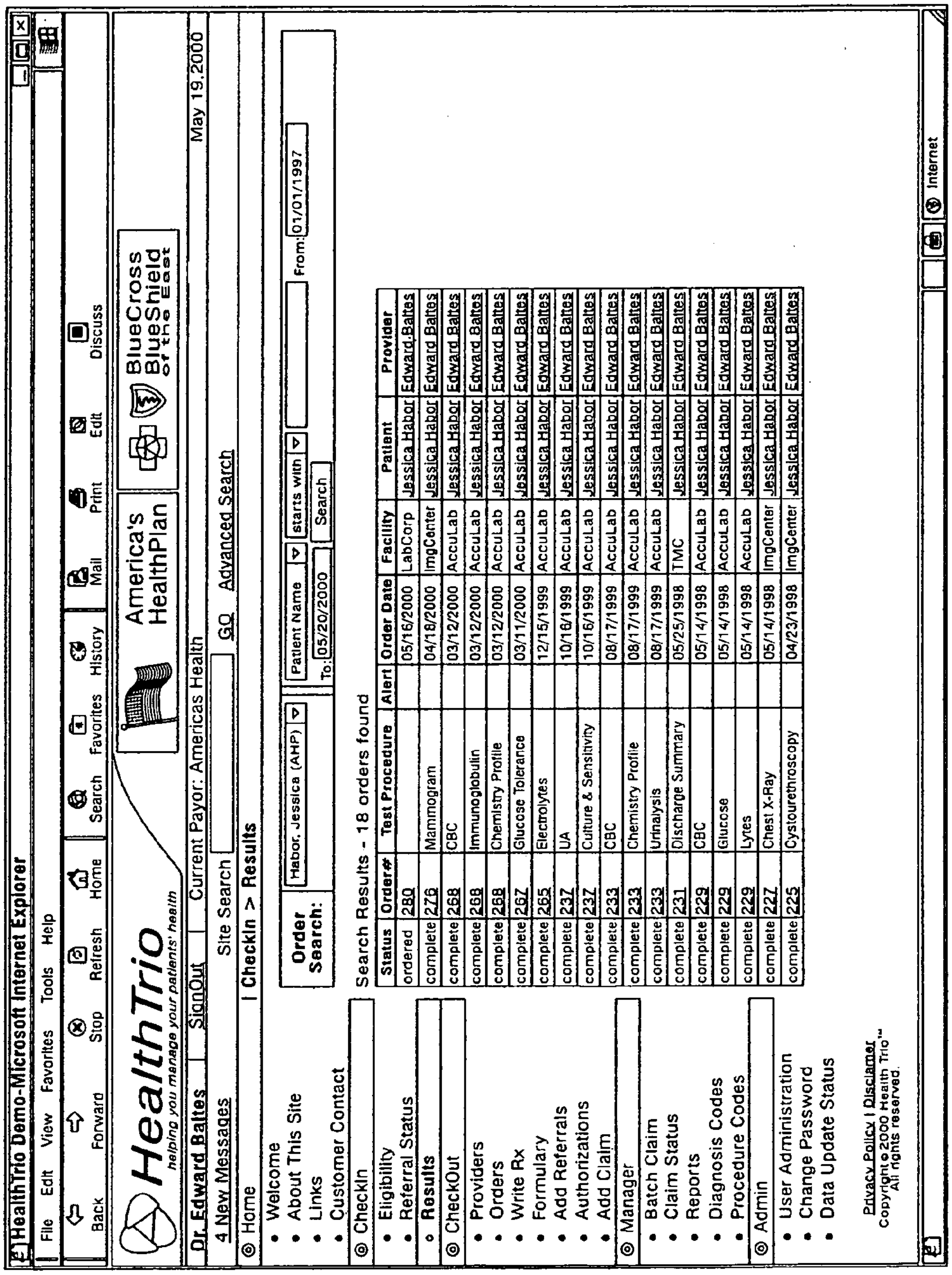
Figure 6C:
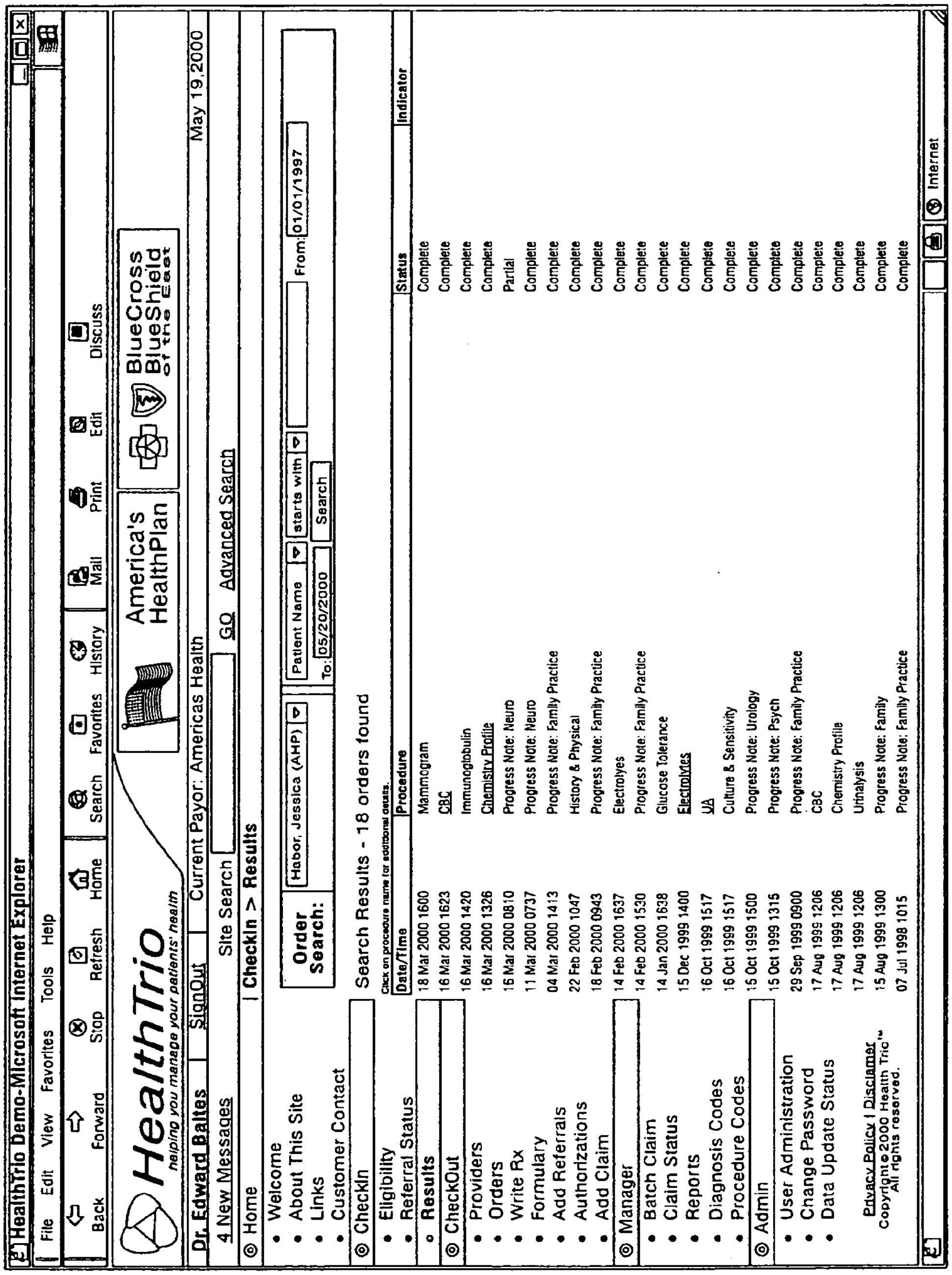
Figure 6D:
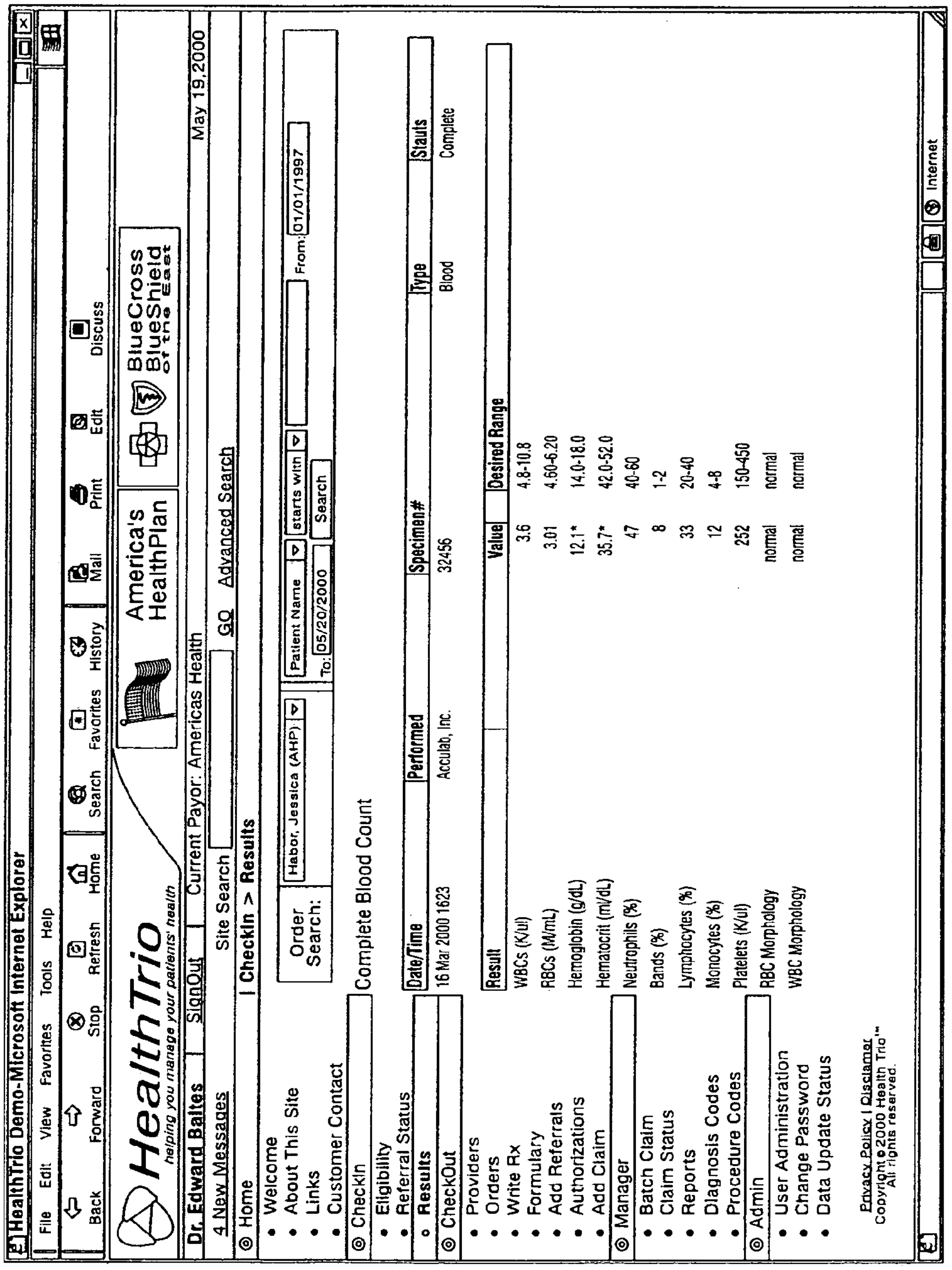

The system's 10 ability to provide personalized information through the portal provides a personalized perspective on patient's health, which tends to hold patient's attention. For patients, this intelligent health care portal becomes the ultimate personalized health site combining both personalized health information based on an individual's claims history, as well as available ancillary (lab, pharmacy, etc.) information and business-to-patient e-commerce, including access to client information, such as eligibility and claims' status. Because of the unique advantage offered to patients, the patient audience can be cost effectively turned into a large number of registered users in a short period of time. In some cases, patients may view communications from physicians through the portal. FIGS. 5A-5C show an example portal from which a patient can obtain and submit information.

The personalized health record typically includes family history, medical profile, test and exam results released by the provider to the patient. The information in the personalized health record may only be released to viewers authorized by the patient. Neither the insurance providers nor family members will have access to the patient's medical information unless the patient specifically authorizes access. As used herein, the terms "patient," "consumer" and "member" are used synonymously.

Figure 2:
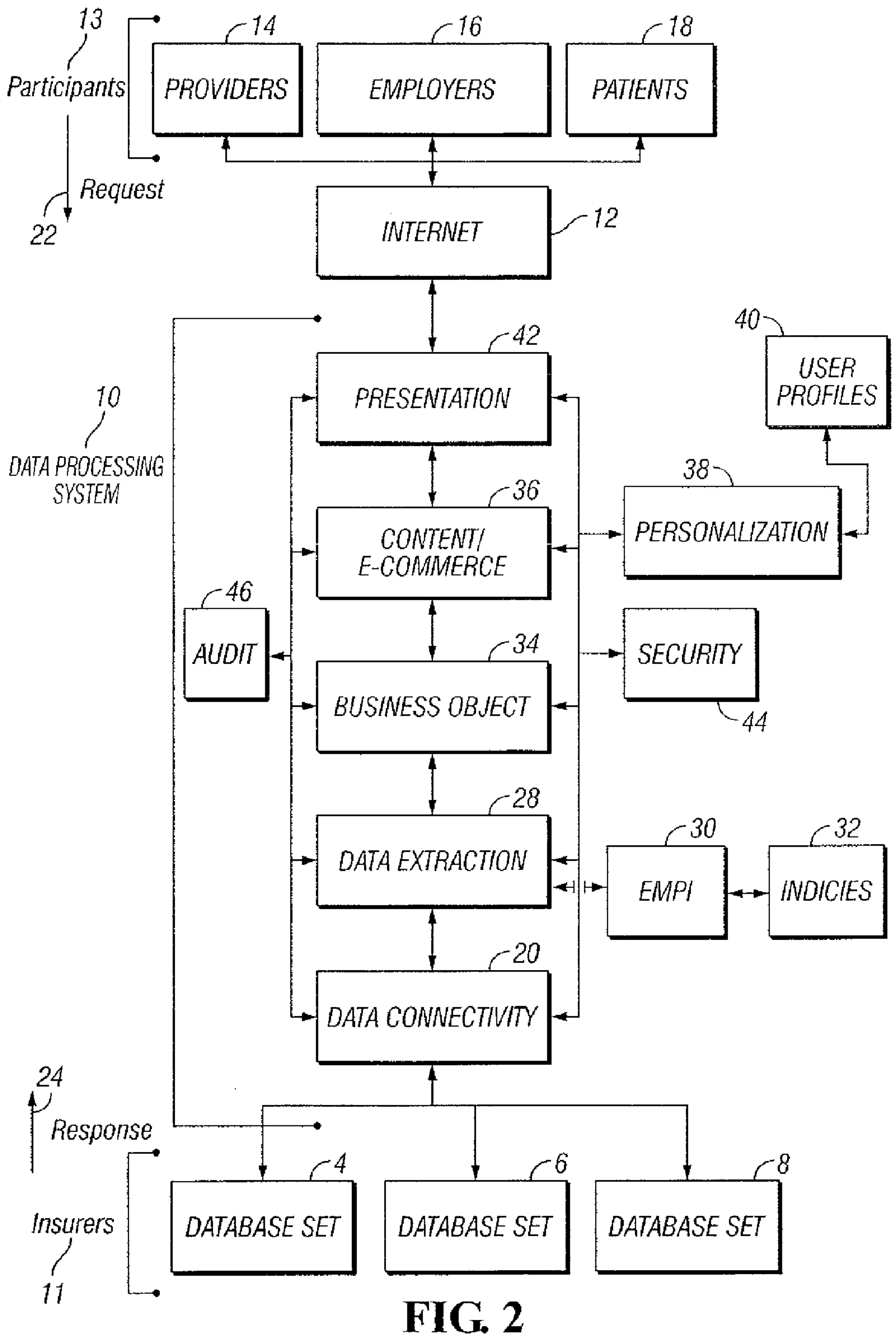
FIG. 2 is a diagrammatic view of the data processing system for the system of normalization shown in FIG. 1.

The architecture of the data processing system 10 is shown in FIG. 2. Each of the database sets 4, 6, 8 is operatively connected to data connectivity sub-system 20. The data connectivity sub-system 20 is configured to receive the different types of connections used between the various computer systems which store the database sets 4, 6, 8. It is appreciated that, in other embodiments, a separate data processing system 10 may be provided at the site of each of the database sets 4, 6, 8 such that each data processing system 10 is dedicated to manage and normalize the data, as discussed further herein, as well as manage server-to-server communications for a single database set.

The data extraction sub-system 28 is also depicted in FIG. 2. Sub-system 28 manages the integration of the often plurality of databases. The data extraction sub-system 28, as further discussed in reference to FIG. 3, also includes logic to manage data access from the several databases of database sets 4, 6, 8. An enterprise master person index ("EMPI") 30 is operatively coupled to data extraction sub-system 28. The EMPI 30 presents a cross-database view of all the insureds within system 2. It also manages the proper identification of providers 14, employers 16, connected patients 18, as well as other entities having unique identities on an as-needed basis. An indices database 32 is supported by EMPI 30. Specifically, the indices database 32 stores indices which serve as a basis for relating the identification data to each other. The indices database 32 is typically built upon and maintained by the EMPI 30.

The business object sub-system 34 contains the logic rules that drives the normalization of data and use of same between insurers 11 and participants 13. To provide such capabilities, a variety of processes may be supported in any particular situation. Illustratively, such processes may include, but are not limited to, rules-based evaluation of entered data for referral authorizations and admission pre-certifications; proxy or actual adjudication of claims submitted by providers, with concomitant delivery of funds to insurers 11 and benefits explanations to patients 18; sorted lists of providers 14, employers 16, and patients 18; and graphical displays of laboratory results and integrated claims-driven health records for patients 18.

The content/e-commerce sub-system 36 adds third party capabilities to the data processing system 10. The content portion of sub-system 36 provides management and integration of third party affiliated content, such as articles about diseases, bulletins, notices, notes, and other medically-related references. The e-commerce portion of sub-system 36 integrates e-commerce capabilities, including business-tobusiness or business-to-consumer purchasing through shopping cart-type databases with affiliated product and service vendors.

The personalization sub-system 38 integrates information from the previous sub-systems 20, 28, 34, 36 to provide a personalized view of data in system 2. Specifically, when any of the participants 13 login to system 2 and access data or other information from database sets 4, 6, or 8, or even the content/e-commerce sub-system 36, pertinent information derived from the type of content viewed, as well as the products purchased or searched, is maintained in a user profile database 40. During subsequent logins, therefore, the information a particular user views can be arranged and accessed in a more familiar, relevant, and useful manner, individual to that participant.

The presentation sub-system 42 manages the normalized data and information into a presentable format for participants 13. For example, the world-wide-web, being a popular destination for users of the internet, accepts output in HTML format, and is accessible by a conventional internet browser. It is appreciated, however, that such data may be presented in virtually any form to accommodate different access devices (for example, WAP for mobile devices).

A security sub-system 44 is shown in FIG. 2 integrated with the other sub-systems 20, 28, 34, 36, 38, 42. Security sub-system 44 maintains data security in several ways. First, one embodiment contemplates that the insurers' 11 data is maintained on its own on-site database, and is controlled by the insurers 11. Second, the insurers' 11 data is encrypted when it is routed from the insurers' 11 database to the connectivity sub-system 20 and, ultimately, the participants 13 when a request 22 is made. Third, the participants' 13 browser includes encryption to view or send data over the internet 12. Finally, internal security is built into the data processing system 10 to only allow users with need-to-know access to particular data, such as claims and referral information. For example, providers 14 may have access only to claims and referral information of their insurers, but not individual claim summaries of their patients. Similarly, the employers 16 may have access to only their employees' claims information, but not some personal information.

An example of an encryption method is the 128 bit Secure Sockets Layer (SSL) with a key certified by VeriSign, Inc. Such SSL encryption means that data traveling through the internet and to participants' 13 browser cannot be interpreted by anyone between those two locations. Encryption is also useful because of the storage of user passwords. There is no place that a user's password is saved or used by the system as traditional clear text. From one of the participants' 13 browser through internet 12 and to one of the insurers' 11 computer or server, the password is protected by SSL. Once the password reaches the final destined server, a cryptographic algorithm converts the password to a protected format. No one, therefore, who has privileged access to the server or any of the back-end applications can get any user passwords.

In addition, encryption is useful along the operative connection to an insurer's 11 database sets 4, 6, or 8 to the data processing system 10. It is contemplated, however, that insurers' 11 computers or servers (database sets 4, 6, or 8) may not need such encryption along this operative connection, if the connection is a true point-to-point connection. Also, this encryption can be implemented through hardware or software, a virtual private network (VPN), or through the use of encryption protocols in a database, for example.

There are several modes with which data can be restricted, even within and among the insurers 11 and participants 13 of system 2. For example, security sub-system 44 may restrict the actual data that a participant 13 may request or view from any of insurers 11. A health care organization, thus, may only view data that they have provided. For example, doctors may only view claim data for their own patients. Alternatively, security sub-system 44 may restrict access to participants 13 to allow access to only particular fields on a particular screen of any particular database. For example, if a screen listed dollar amounts for claims, employers may wish to restrict who is able to view those dollar amounts. Other users, therefore, like patients 18, might be able to see the rest of the claims, but not the dollar amounts. Still, further, security sub-system 44 may restrict which screens will be accessible to which users. This level of security defines which functionality is available to the user. For example, a patient 18 in system 2 may not be able to view the claim submittal screen submitted by provider 14 at all, but may view a diagnosis information or health plan administrative screen. Customizable security based on the interests of the user may be included as well. This security method allows either the insurers 11 or participants 13 to set the parameters of security for the examples described above. It is further contemplated that this tool may be an internet-based tool that could add logins to the system, as well as specify values and screens that a particular user has access to. It is still further contemplated that a portion or all of the security measures can be employed throughout data processing system 12.

HealthTrio's eHealthManager maintains data security in multiple ways. First, the payor's data resides on its own on-site database, and is controlled by the payor. Second, the payor's data is encrypted when it is routed from the payor's database to the Web server. Third, the user's Web browser must be upgraded to the highest strength of encryption to view or send data over the Web. A link to upgrade the user's browser at no cost is available. Finally, internal security is built into the application to only allow users with a need to know—access to data such as claims and referral information. For example, providers will have access only to their claims and referral information and authorized employer users access to their employees' information.

In addition, personal health information that a member enters in HealthTrio's eHealthManager will only be released to viewers authorized by the member. Neither the health plan, nor any unauthorized physicians or family members will have access to a member's medical information unless the member specifically authorizes access.

HealthTrio maintains data security by applying internal application security. This limits user access to health plan data on a need-to-know basis, allowing health plans to control their data on-site by the health plan and using the most current network encryption technology.

Data—This level of confidentiality restricts the actual data that a user may view from the database. A health care organization may only view data that they have provided. Doctors may only view claim data for their own patients, etc. . . .

Field—This level of security allows users to view additional pieces of information on a particular screen. For example, if a screen listed dollar amounts for claims, organizations may wish to restrict who is able to view that piece of data. The user would be able to see the rest of the table, but the dollar amount of the claim would be hidden.

Screen—This level of security defines which functionality is available to the user. For example, a patient in the system may not be able to view the claim submittal screen at all.

Administration—This portion of the confidentiality model is a web-based tool that allows the customer to set security in the other 3 levels shown above. This tool would be a web-based tool that could add logins to the system, as well as specify values and screens that a user has access to.

HealthTrio uses encryption between the web server and each doctor's office. The encryption is 128 bit SSL with a key that is certified by VeriSign. SSL encryption for this piece means that the data that travels from the web server to the user's browser cannot be interpreted by anyone along the way from the web server to the user's browser. The other benefit gained from SSL (and resulting from the VeriSign certification) is the authentication of the connect site to the doctor. The user can read the name and identifying information that is an integral part of the key, see that it has been certified by a major certifying authority, and know that he is truly attached to the HealthTrio site and not an imposter site. SSL is the industry-standard form of encryption for the web and is used by many sites including most all credit card shopping carts and banking/financial web applications.

The second use of strong encryption practices is built into the storage of user passwords. There is no place that a user's password is saved or used by the system as cleartext. From the user's browser to the web server, the passphrase is protected by SSL. Once at the web server a cryptographically strong algorithm converts the password to a protected format. Nobody who has privileged access to the web server or any of the back-end application can get any user passwords.

The third use of encryption is along the link from the payor's database to the web server. Note that at the current time, payors may not be required to use encryption along this link if the connection is a true point-to-point connection (point-to-point is the preferred and most reliable method of connecting a payor and the centrally located application). This encryption can be implemented through a hardware or software VPN (virtual private network) or through the use of the database driver's built in encryption protocols. Hardware VPN is the best in terms of speed and the database encryption is perhaps the quickest, but also least flexible, means of securing the line.

One of the most important facts to success for e-business applications, such as HealthTrio connect, is the capability to limit each customer to the information they have privileges to view. This portion of the system might be termed "confidentiality," since it pertains to restricting access to customer data by users. This document outlines the confidentiality model for connect.

There are 5 main considerations that the model addresses:

1. Data—This level of confidentiality restricts the actual data that a user may view from the database. A health care organization may only view data that they have provided. Doctors may only view claim data for their own patients, etc. . . .
2. Field—This level of security allows users to view additional pieces of information on a particular screen. For example, if a screen listed dollar amounts for claims, organizations may wish to restrict who is able to view that piece of data. The user would be able to see the rest of the table, but the dollar amount of the claim would be hidden.
3. Screen—This level of security defines which functionality is available to the user. For example, a patient in the system may not be able to view the claim submittal screen at all.
4. Administration—This portion of the confidentiality model is a web-based tool that allows the customer to set security in the other 3 levels shown above. This tool would be a web-based tool that could add logins to the system, as well as specify values and screens that a user has access to.
5. User Id and Password—This section deals with the vulnerability of user-id's and passwords.

The breadth of the user community for connect is extremely diverse. Therefore, this model must be extremely flexible in its capability to accommodate many types of users, while concurrently adhering to the performance goals of the system. The accompanying pages of this document detail more closely each step of the confidentiality model.

Data Confidentiality Model

As stated above, this level of confidentiality restricts the actual data that a user may view from the database. Since the connect product allows many types of users, such as payors, plan administrators, patients, physicians and specialists, each user type will need to view not only different types and levels of data. For example, a payor will need to view all of the patients and providers in their plan, while a physician group will need capabilities to view all patients in the group for all payors.

To accommodate this complexity, each login is tied to a confidentiality type. Confidentiality types that have been identified so far include payor, provider, provider group, patient, patient group and public. The model is flexible enough to handle additional types as needed. When the user logs into the system, the type of security is polled, as well as values for that type of login. The information that is from the database is then dynamically modified to reflect the users' privileges.

The capability to implement confidentiality can be achieved by storing the type of user associated with a login, as well as a list of valid values that a user is eligible to view. This information would be stored in the Local Application Database (LAD), and would be maintained by an administrator representing the payor, or entered automatically by connect.

The technical implementation of this is dramatically more complex than the above illustration so that administration of these items would be easier. For example, if an administrator had to maintain a list of valid values for each user in the system, a tremendous effort would be required. To ease this burden, the security administration tool allows groups, templates and login duplication.

Screen Confidentiality Model

Screen confidentiality is the ability of the system to restrict users to features of the system that they have been granted privileges to see. While the previous model pertained to which data was to be brought back from the payors system database, this level of confidentiality relates to how the data is displayed and what features of the system can the user exercise on that data.

Another user in the same physicians group may have a completely different toolbar based on security. In this case, the user may not have access to Write Rx, Formulary, Referrals and Authorizations due to organizational constraints.

Field Confidentiality Model

Field confidentiality is the ability of the system to restrict users to fields and features of the system that they have been granted privileges to see. Once a user has been determined to have access to a screen by the previous security module, connect will only show features and fields for that screen that they user has access to.

Security Administration

The combination of data, screen and field confidentiality capabilities provides nearly endless security and flexibility capabilities to the connect product. Essentially, any data that can be captured can also be displayed in a confidential manner over the web to only those users that are specified by an administrator. However, for an administrator to manage each of these items on an individual basis, the task would be HealthTrioal! Therefore, an administration tool has been created to make this ease this burden. 3 features that dramatically decrease the amount a time required to administer the security information are access lists, profiles, and user signup. Each of these is explained in detail below.

Access Lists—An access list specifies which data items a user has access to. In a typical situation, all users from a given organization would share an access list. For example, all connect users from Providence Doctors Group would share an access list named Providence Doctors Group Access List. This access list would specify the data items the users attached to it could view.

Profiles—In addition to an access list, each user in connect has a profile. A profile specifies the screens, fields and functions that a user has access to. A profile typically groups together types of user across organizations, unlike access lists, which group together users in a single organization. For example, an office manager would typically have access to nearly all features in the office, while a data entry clerk may only have access to the claims add portion of the system.

User Signup—The single most time consuming portion of a typical administration task is the initial entry of information for each login in the system. To avoid this task, connect allows the capability for users to signup for the system, specifying requested access lists and profiles in the process. From this signup request, the administrator can then simply deny or accept the application for signup. Upon acceptance of an application, the required information is automatically entered for that user into connect . . . drastically reducing the amount of effort required the administrator to sign up a new user.

User ID and Password

The following features are related to the user id and password vulnerability in the connect system:

Password Failure Account Locking—A payor may select whether or not to lock a user account after a specified number of unsuccessful logins.

Failed Login Tracking—If a specified number of invalid user logins have been specified by a given IP address, the payor is notified and has the option of locking that IP/address from accessing the login screen.

Password shielding—Passwords are always fully encrypted from the time they are captured on the screen to the time validated or failed. Passwords are stored in the database in a one-way hash format, thus nobody has the capability to view the password. The login process itself must re-hash the password on login, then compare to the hashed value in the security tables.

Security Database—The security database can only be queried by the application server and is physically housed in a building secured by key and card access.

User ID shielding—Since connect has the capability of supporting many payors simultaneously, connect does not allow any access by the payor to userids and passwords. All users are referenced by their actual names in the security administration tools . . . login ids are never given out. All password resets and account unlocking is done by the connect help desk after going through a series of questions known only to the user.

Password makeup—The payor may specify the length of a password, as well as whether to require numbers or special characters in the password. If one user has multiple payors, the most stringent payor's rules are used.

Password Expiration—The payor may determine whether or not to force the user to change their password after a specified amount of time.

An audit sub-system 46, like security sub-system 44, shown in FIG. 2, is also integrated with the other sub-systems 20, 28, 34, 36, 38, 42. Audit sub-system 46 tracks the operation of all sub-systems. The information generated from audit sub-system 46 allows an administrator to monitor the operation of system 2 for problems and marketing trends.

Figure 3:
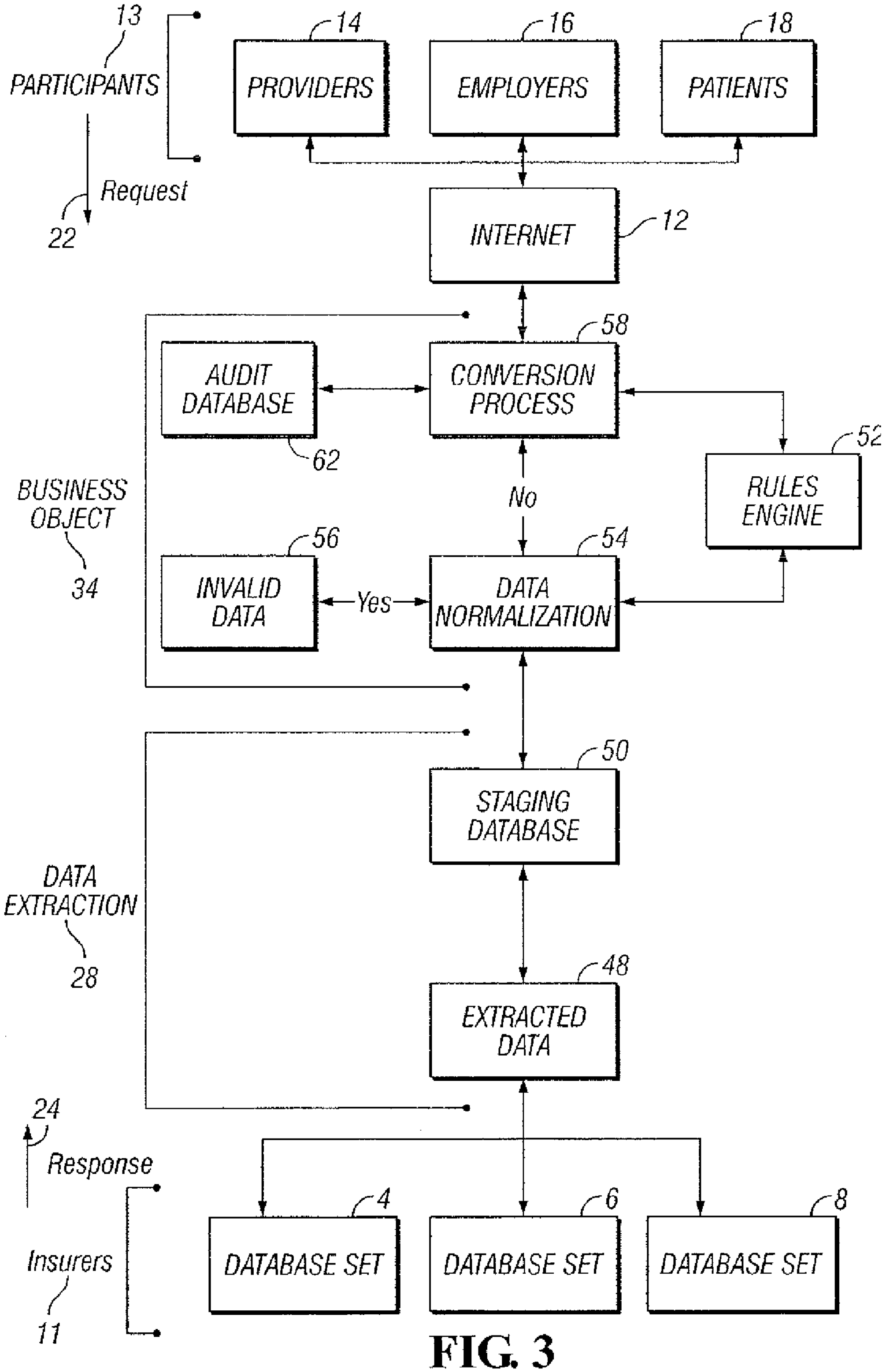
FIG. 3 is a diagrammatic view of the data extraction and business object sub-systems for the system of normalization shown in FIG. 1.

A diagrammatic view of the data extraction and business object sub-systems 28, 34, respectively, is shown in FIG. 3. As previously discussed, the numerous databases represented by database sets 4, 6, 8 contain data in a variety of formats. Before the data is transferred to one of the participants 13, however, it is first formatted to a new format that is readable by any of the computers of participants 13, like HTML format, for example. The data is, therefore, "extracted" from the database sets, either 4, 6, or 8, and then "normalized" to be read by the computers of participants 13. The extracted data is indicated by reference numeral 48.

Extracted data 48 from either database sets 4, 6, or 8 is uploaded to a staging database 50 which is typically a portion of data extraction sub-system 28. Rules engine 52 serves a dual purpose of defining the rules that control the normalization of the data, as well as how the data, once normalized, is used. During the normalization process at 54, rules engine 52 homogenizes the data by determining what the data means, then inserting the data into the proper field as normalized data. Rules engine 52 also remodels the data, if necessary, to a structure or appearance predefined by the normalized format. As a simple example, in a referrals database that may hypothetically exist on database set 6, it may include the entry "New Jersey" in the state location field. If that field is requested by a participant 13, the rules engine 52 will cause that field to be extracted, then determine whether the meaning of this field corresponds to the meaning of the normalized state location field, and, if so, then convert the field to the normalized state location field at 58. Furthermore, if the rules engine 52 has predetermined that the normalized state location field should exist as only a two-character acronym, then the phrase "New Jersey" will be remodeled to the acronym "NJ." This is contrasted with traditional transliterating programs that would merely match the state location field of the referrals database with any field in another database titled "state location field" and then transfer the data. Such a program cannot determine the meanings of the state location fields, and then determine if their meanings matched, as well as not remodel the data to the appropriate appearance. For example, a field for laboratory enzymes might be expressed in Celcius in one database and in Fahrenheit in another database. Such data, as well as countless other data, are typically contextualized by the system they exist in. Transliterating programs do not compensate for such context among data. In the present disclosure, part of the normalization is determining the meaning of the data and locating it in a field of the same definition, but in a single format.

Rules engine 52 also determines whether the data is bad or invalid. Any bad or invalid data that is discovered during the normalization process at 54 is transferred to an invalid data database 56. Invalid data is placed in database 56 for review and appropriate corrective action and, if appropriate, reintroduced and normalized.

In addition, the rules engine 52 incorporates security 44 to determine whether the requestor has authorization to view the data that is being requested, as previously discussed. For example, if employer 16 requests claims data that illustratively exists on database set 8, the rules engine 52, in conjunction with the security 44, determines whether employer 16 has authorization to view the data subject of that request. If not, rules engine 52 would deny fulfillment of the request.

Once the data is converted and remodeled into the normalized format, rules engine 52 determines how the normalized data can be used. For example, if a request 22 is made from providers 14 to one of the insurers 11 to authorize a chest X-ray for one of the patients 18, a proper response 24 may reference data from various eligibility, claims, benefits, and personal data databases which rules engine 52 first extracts and normalizes. Once the data is normalized, rules engine 52 undertakes the process of responding to request 22. Rules engine 52 bases response 24 on predetermined rules established by the particular insurer 11 to determine whether a chest x-ray is an approved procedure in response to the request. It is contemplated that each insurer 11, or even each database set 4, 6, 8 can be subject to its own unique set of rules to govern any particular response 24.

An audit database 62, illustrated in FIG. 3, manages and maintains tracking information during the conversion process at 58. All data requests, responses, and e-commerce submissions can be monitored and recorded. This audit trail information is maintained in audit database 62 to enhance performance and security characteristics. It is contemplated that audit database 62 can be integrated with audit sub-system 46, as shown in FIG. 2, or database 62 can be a stand-alone system working independently or in addition to sub-system 46.

Figure 4:
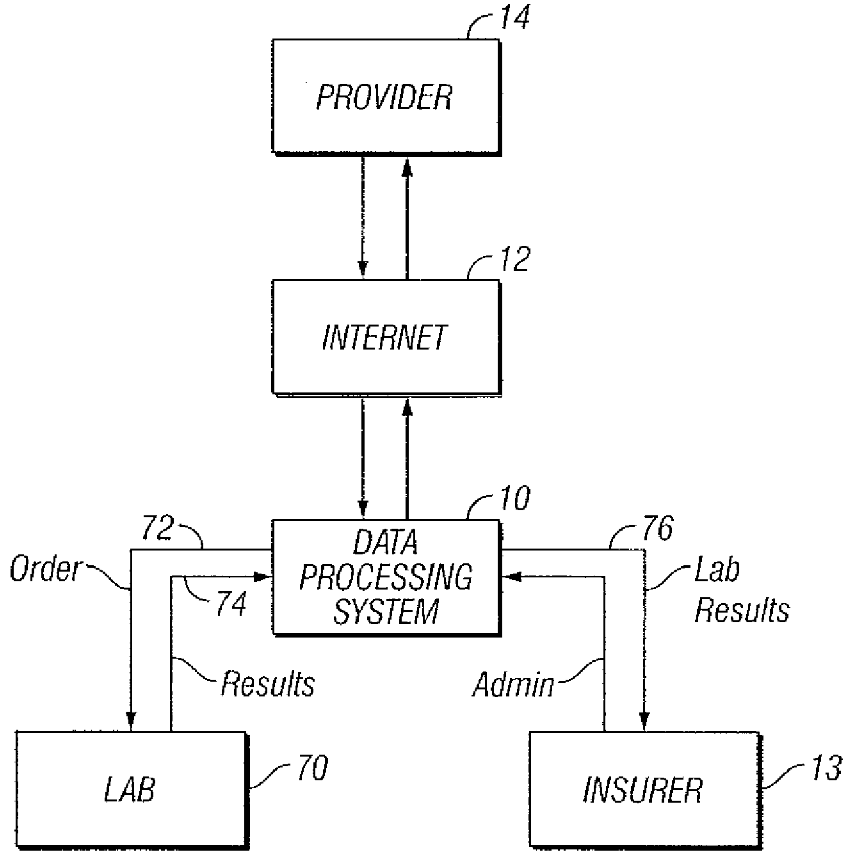
FIG. 4 is a diagrammatic view of a system of health care management for medical testing between health care insurers and participants.
Figure 7:
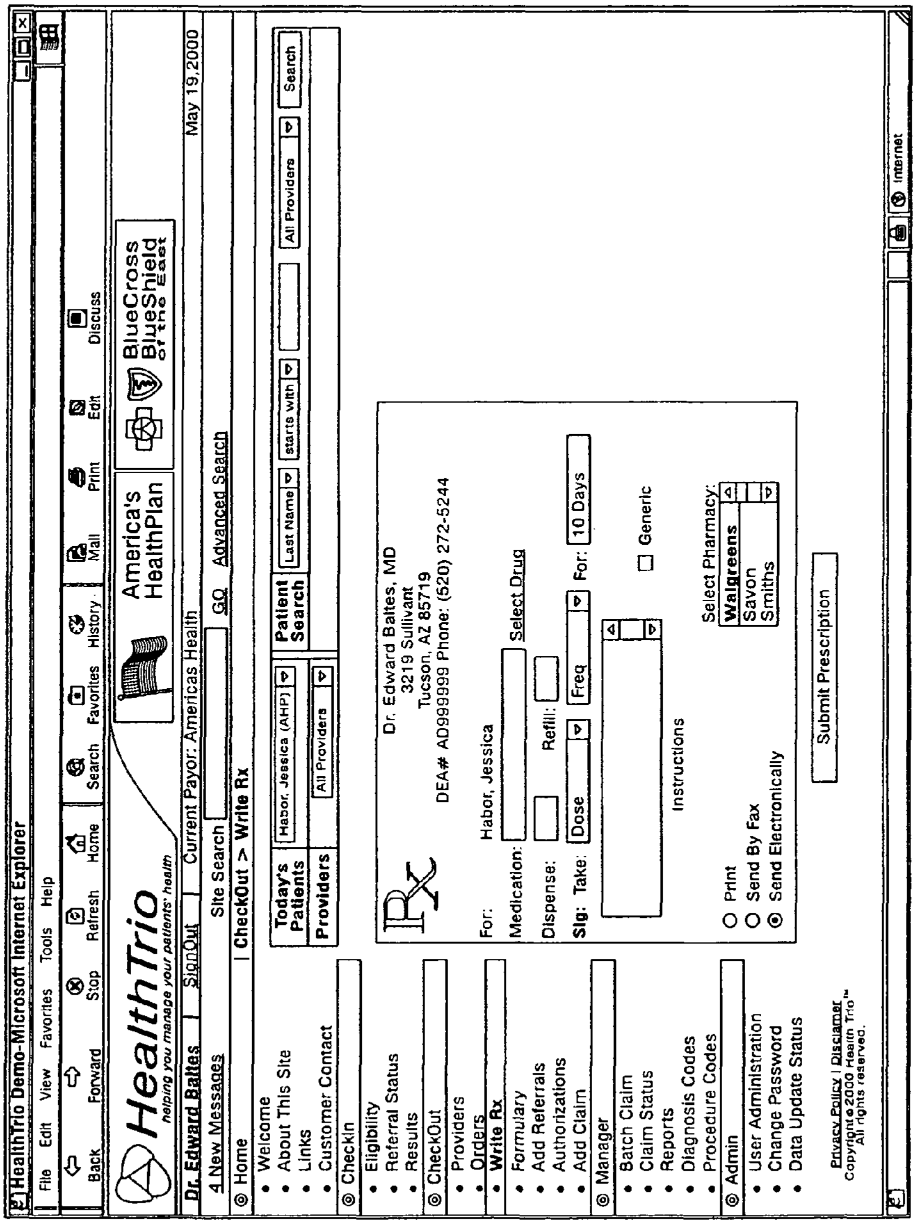
FIG. 7 shows an example user interface in which a health care provider can submit a prescription to a pharmacy over the Internet.

In one embodiment of the disclosure, it is contemplated that system 2 will not only exchange information related to insurance and payment issues, but also provide active management of patient care. For example, as shown in FIG. 4, a portion of system 2 depicts the process for medical tests to be ordered, approved, and results submitted. For example, a health care provider 14, via the internet 12, places an order for a medical test. The order is transmitted through data processing system 10. The order is further transmitted at 72 to a laboratory 70, the order will disclose particular information that will be needed when either the specimen or the patient arrives. If a specimen is collected by provider 14, the order will identify the laboratory 70, and provide information to provider 14 so that the specimen may be marked accordingly before being sent to laboratory 70. Once laboratory 70 receives the order and the specimen, laboratory 70 can either communicate the status or results back through data processing system 10 to both the provider 14 and the appropriate insurer 13', as indicated by reference numerals 74, 76, respectfully. FIGS. 6A-6D show an example user interface for health care providers to order and view medical tests. FIG. 7 shows an example user interface in which a health care provider can submit a prescription to a pharmacy over the Internet.

Although the system has been described with reference to particular means, materials and embodiments, from the foregoing description, one skilled in the art can easily ascertain the essential characteristics of the illustrative system and various changes and modifications may be made to adapt the various uses and characteristics without departing from the spirit and scope of the present invention as described by the claims which follow.

What is claimed is:

1. A computerized method for facilitating an exchange of information between a patient and a health care provider, the method comprising the steps of:

providing a database having stored electronic health records of a plurality of patients, wherein the health records of the patients are maintained and used by at least one health care provider of the patients in the regular care of the patients;

establishing a connection using a network between a computer system of a health care provider and the database;

receiving a selection of a patient from the plurality of patients from the health care provider through a provider user interface;

receiving a request from the health care provider for at least a portion of a health record of the selected patient through the provider user interface;

retrieving the requested health record of the selected patient from the database and displaying at least a portion of the requested health record on the provider user interface;

receiving a provider entry regarding clinical care of the selected patient from the health care provider through the provider user interface, wherein the provider entry comprises one or more of a physician's note, a physician assistant's note, laboratory results, imaging results, test results, or a medication concerning the selected patient;

storing on the database the provider entry in the health record of the selected patient;

establishing a secure connection via the Internet between a computer system of the selected patient and the database;

receiving a request from the selected patient via the secure connection for at least a portion of the selected patient's health record through a patient user interface, wherein the patient user interface is a web browser interface, and wherein the patient user interface provides access to the selected patient's health record;

retrieving the health record of the selected patient from the database and displaying at least a portion of the health record on the patient user interface, wherein at least the provider entry made by the health care provider regarding clinical care of the selected patient is displayed on the patient user interface, wherein the provider entry displayed on the patient user interface comprises one or more of a physician's note, a physician assistant's note, laboratory results, imaging results, test results, or a medication concerning the selected patient;

displaying one or more of content or a link for content on the patient user interface that explains or assists the selected patient regarding one or more of a condition, procedure or medication in the selected patient's health record, wherein the content or link for content is selected based on information contained in the selected patient's health record;

receiving a patient entry regarding a health care parameter of the selected patient from the selected patient through the patient user interface;

storing on the database the patient entry in the selected patient's health record;

responsive to a request by a health care provider via the provider user interface for the health record of the selected patient subsequent to the patient entry, displaying the patient entry on the provider user interface;

receiving an access list from the selected patient via the patient user interface over the Internet, wherein the access list is indicative of access rights to at least a portion of the selected patient's health record;

receiving on a computer a new request for at least a portion of the selected patient's health record from a second health care provider of the selected patient via the provider user interface;

detecting on a computer whether the second health care provider has been granted access to the selected patient's health record based on the access list;

transmitting the selected patient's health record to the second health care provider responsive to the detecting step; and wherein the access list includes a first set of access rights associated with the health care provider and the second health care provider and a second set of access rights associated with one or more family members of the selected patient.

2. The method of claim 1, wherein the patient entry is selected from the group consisting of family health history of the patient and over-the-counter medications taken by the patient.

3. The method of claim 2, further comprising the step of auditing access to the personal health data.

4. The method of claim 1, wherein at least a portion of the information in the database provided by the health care provider is developed by extracting health care data from a separate database and normalizing the extracted data to a predefined format in accordance with a rules engine that defines a plurality of health care data fields in a predefined format and a plurality of relationships between fields of normalized data.

5. The method of claim 1, wherein the patient user interface includes an interface element indicative of current medications taken by the selected patient, further comprising the steps of receiving a selection from the selected patient of the interface element to view current medications in the selected patient's health record, retrieving the selected patient's current medications from the database, and displaying the current medications of the selected patient on the patient user interface.

6. The method of claim 5, wherein the current medications include prescriptions from a health care provider entered via the provider user interface and over-the-counter medications entered by the selected patient via the patient user interface.

7. The method of claim 5, wherein the patient user interface includes an interface element indicative of discontinued medications of the selected patient, further comprising the steps of receiving a selection from the selected patient of the interface element to view discontinued medications in the selected patient's health record, receiving the selected patient's discontinued medications from the database, and displaying the discontinued medications of the selected patient on the patient user interface.

8. The method of claim 5, further comprising the steps of receiving a selection from the selected patient of one or more of the current medications via the patient user interface and receiving a selection from the selected patient to renew the selected medications.

9. The method of claim 8, further comprising the step of receiving a selection from the selected patient via the patient user interface to check interactions of one or more of the current medications in the selected patient's health record.

10. The method of claim 5, further comprising the step of receiving a patient entry regarding an allergy of the selected patient through the patient user interface.

11. The method of claim 1, wherein the content or a link for content is a health maintenance remainder based on the selected patient's health record.

12. The method of claim 1, further comprising the step of receiving a secure message from the selected patient to a health care provider via the patient user interface and sending the secure message to the health care provider.

13. The method of claim 12, further comprising the step of receiving a secure message from a health care provider of the selected patient to the selected patient via the provider user interface and sending the secure message to the selected patient.

* * * * *